United States Patent [19]

Lewellyn

[11] 4,456,560
[45] Jun. 26, 1984

[54] PROCESS FOR THE PREPARATION OF N-ALLYL-O-ALKYL THIONOCARBAMATES

[75] Inventor: Morris E. Lewellyn, Bridgeport, Conn.

[73] Assignee: American Cyanamid Company, Stamford, Conn.

[21] Appl. No.: 410,773

[22] Filed: Aug. 23, 1982

[51] Int. Cl.$^3$ .......................................... C07C 155/02
[52] U.S. Cl. ............................................... 260/455 A
[58] Field of Search ................................... 260/455 A

[56] References Cited

U.S. PATENT DOCUMENTS 2,462,433  11/1963  Searles ............................ 260/455 A Primary Examiner—Henry R. Jiles
Assistant Examiner—Robert C. Whittenbaugh
Attorney, Agent, or Firm—Michael J. Kelly

[57] ABSTRACT

An improvement in the process for the preparation of N-allyl-O-alkyl thionocarbamates by the reaction of an allyl isothiocyanate with an alcohol is disclosed which comprises the use of a catalyst of the general formula:

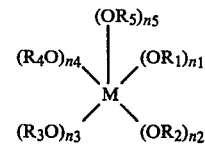

wherein $R_1$, $R_2$, $R_3$, $R_4$, and $R_5$ are individually selected from alkyl or aryl or a mixture thereof, M represents a metal from Group III B, IV B, or V B of the Periodic Table of the Elements, and n is the integer 0 or 1; provided that the sum of $n_1$, $n_2$, $n_3$, $n_4$, and $n_5$ equals the valance of said metal M.

12 Claims, No Drawings

PROCESS FOR THE PREPARATION OF N-ALLYL-O-ALKYL THIONOCARBAMATES

The present invention relates to an improved process for the preparation of N-allyl-O-alkyl thionocarbamates by the reaction of an allyl isothiocyanate with an alcohol in the presence of an improved catalyst.

N-allyl-O-alkyl thionocarbamates, and in particular N-allyl-O-isobutyl thionocarbamate, are useful promoters for sulfide ore floatation, which use is disclosed in a commonly assigned, copending application, Ser. No. 06/309,851, filed Oct. 8, 1981.

The preparation of thionocarbamates by the reaction of an organic isothiocyanate with an aliphatic alcohol in the presence of either ferric acetylacetonate or dibutyl tin dilaurate catalyst is known; see Iwakura et al, Can. J. Chem 40, 2359–2375 (1962). Ferric acetylacetonate and dibutyl tin dilaurate do indeed catalyze the reaction, affording the thionocarbamates in good yield; but, when allyl isothiocyanates are used in the reaction, large amounts of catalyst are required and at least a 1.5:1 mole ratio of alcohol to allyl isothiocyante is needed. The use of large amounts of catalyst is uneconomical and the use of a large excess of alcohol necessitates its recovery by vacuum stripping when the reaction is completed.

These and other disadvantages of the prior art processes are ameliorated by applicants discovery of an improved process, the improvement comprising the use of an improved catalyst represented by the general formula:

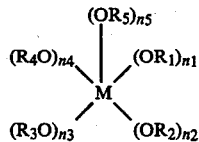

wherein $R_1$, $R_2$, $R_3$, $R_4$, and $R_5$ are individually selected from alkyl or aryl or a mixture thereof, M represents a metal selected from Group III B, IV B, or V B of the Periodic Table of the Elements, and n is the integer 0 or 1, provided that the sum of $n_1$, $n_2$, $n_3$, $n_4$, and $n_5$ equals the valance of said metal.

This and other advantages of the instant invention will become more readily apparent in the detailed description which follows.

The present invention is based on the discovery that the aforementioned catalysts are highly efficient catalysts for the preparation of N-allyl-O-alkyl thionocarbamates.

The advantages realized by their use are (1) higher conversion of the isothiocyanate to thionocarbamate, (2) higher purity of the resulting product, (3) elimination of the need for and recovery of a large excess of alcohol, (4) shorter reaction times, and (5) reduced catalyst usage.

In accordance with the present invention, an allyl isothiocyanate is reacted with an alcohol in the presence of a catalytic amount of the catalyst compound, generally by heating the reaction mixture at a temperature and for a period of time sufficient to convert the allyl isothiocyanate to the N-allyl-O-alkyl thionocarbamate. Preferably the temperature is in the range of about 100° C. to 120° C.

Allyl isothiocyanates which are preferably employed in the process of the instant invention are those represented by the formula:

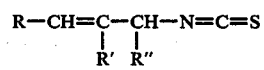

wherein R, R', and R" are individually selected from hydrogen, alkyl (preferably 1 to 20 carbon atoms), aryl or alkyl substituted aryl.

In a preferred embodiment of the invention, R, R', and R" are individually selected from hydrogen and lower ($C_1$ to $C_4$) alkyl groups, and in an especially preferred embodiment, R, R', and R" are individually selected from hydrogen and methyl. Particularly preferred species of isothiocyanate are allyl isothiocyanate and methallyl isothiocyanate.

The allyl isothiocyanates may be prepared by known methods disclosed in the literature; see, for example, Searles, U.S. Pat. No. 2,462,433; Bentz et al, German Offen. No. 2,711,956; Reeves et al, Synthetic Communications 6 (7), 509–514 (1976).

The preparation of allyl isothiocyanates, according to an improved process which utilizes a phase transfer catalyst in the reaction of an aqueous solution of an alkali metal or ammonium thiocyanate with an allyl halide, is described in a commonly assigned, copending application, Ser. No. 410,689, filed Aug. 23, 1982, the disclosure of which is incorporated herein by reference thereto.

The alcohols which are useful in the instant invention are preferably aliphatic primary and secondary alcohols, and particularly linear or branched chain primary alcohols, containing from 1 to 20 carbon atoms, the carbon chain of which may be interrupted by a hetero atom (O, S, or N).

In a preferred embodiment, linear or branched chain primary alcohols containing 1 to 5 carbon atoms are used. These alcohols include methanol, ethanol, n-propanol, n-butanol, isobutanol, n-amyl alcohol, 2-methylbutanol-4, and 2,2-dimethylpropanol-1. Isobutanol is particularly preferred.

Other alcohols which may be used to prepare thionocarbamates in accordance with the process of the invention include isopropanol, sec. butyl alcohol, 2-methoxyethanol, 2-ethoxyethanol, 2-(2-n-butylethoxy)ethanol, 2-(2-methoxyethoxy)ethanol, diethylene glycol, triethylene glycol, and ethylene oxide polymers:

wherein x is an integer from about 4 to about 20, examples of which include Carbowax 200, Carbowax 400, Carbowax 600, and the like.

Ferric acetylacetonate and dibutyl tin dilaurate, which have been disclosed as catalysts for the reaction of alkyl isothiocyanates with alcohols (Iwakura et al, supra), are examples among many which are known to be effective catalysts for the reaction of alcohols with organic isocyanates; see Britain and Gemeinhardt, J. Appl. Poly. Sci. 4, 207–211 (1960). Among the many catalysts which are disclosed therein, many are deficient catalysts for the reaction of allyl isothiocyanates with alcohols; for example, ferric chloride, potassium oleate, bismuth nitrate, and tertiary amines. Tetraalkyl titanates and tetraalkyl zirconates were found to be superior catalysts for the reaction of allyl isothiocyanates with alcohols, as compared with the known catalysts—ferric acetylacetonate and dibutyl tin dilaurate.

When the subject reaction is conducted using an excess of the alcohol, for example, at a mole ratio of allyl isothiocyanate to alcohol of 1:2, conversion of the allyl isothiocyanate to thionocarbamate is significantly lower with ferric acetylacetonate than it is with an equal concentration of tetraalkyl titanate, for example. Surprisingly, however, when the reaction is conducted with a 1:1 molar ratio of allyl isothiocyanate to alcohol, the tetraalkyl titanate catalysts provide markedly higher conversion to thionocarbamate than ferric acetylacetonate. Moreover, it is found that tetraalkyl titanates and tetraalkyl zirconates afford the thionocarbamates in significantly higher purity, indicating that side reactions are reduced or eliminated. Finally, it was found that higher conversion to thionocarbamate and higher purity thereof are realized with a lower catalyst concentration of the tetraalkyl titanate or tetraalkyl zirconate catalysts than with the known catalysts, particularly when the mole ratio of allyl isothiocyanate to alcohol is equimolar. As indicated above, the increased efficiency of the catalysts provide the additional advantage that the need for the use of excess alcohol is eliminated; therefore, the need for recovery of the alcohol thereby simplifies the process.

The catalyst compounds, which are usefully employed in the present invention, are those represented by the formula:

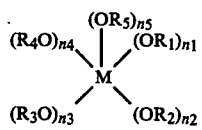

wherein $R_1$, $R_2$, $R_3$, $R_4$, and $R_5$ are individually selected from alkyl or aryl or mixtures thereof, M represents a metal from Group III B, IV B, or V B of the Periodic Table of the Elements, and n is the integer 0 or 1, provided that the sum of $n_1$, $n_2$, $n_3$, $n_4$, and $n_5$ equals the valance of said metal.

In a preferred embodiment of the invention, M is a metal from Group IV B of the Periodic Table, n is 4 and the R groups are alkyl of 1 to 8 carbon atoms. Especially preferred catalysts include tetraalkyl titanates and tetraalkyl zirconates, and particularly preferred catalysts are the tetraalkyl titanates, examples of which include tetra-n-butyl titanate, tetraisopropyl titanate, and tetra-2-ethylhexyl titanate.

Other catalysts which may be used are those wherein M is scandium, yttrium, lanthanum, hafnium, vanadium, niobium and tantalum and wherein n may have a value from 2 to 5. Especially useful are those wherein the metal is niobium, vanadium and lanthanum, for example, niobium phenoxide, lanthanum isopropoxide, and vanadyl n-butylate.

The catalysts may be used in the reaction in an amount ranging from about 0.01 to 4 mole percent, based on the isothiocyanate. Preferably, the catalysts are used in an amount of from about 0.1 to 1.0 mole percent, same basis.

Although the present invention relates to improvements in the process for the preparation of N-allyl-O-alkyl thionocarbamates by the reaction of an allyl isothiocyanate and an aliphatic alcohol and although the allyl isothiocyanate source is unimportant, it is preferred that the preparation of the N-allyl-O-alkyl thionocarbamates be prepared according to a unitary process whereby the allyl isothiocyanate is initially prepared by reaction of an allyl halide with an aqueous solution of an alkali metal or ammonium thiocyanate under the influence of a phase transfer catalyst. Such processes are described in the aforementioned commonly assigned, copending application, Ser. No. 410,689, filed Aug. 23, 1982, and in another commonly assigned, copending application, Ser. No. 410,687, filed Aug. 23, 1982. When the unified process is used, the allyl isothiocyanate produced may be dried by azeotropically distilling trace amounts of water and the reaction is continued, as described herein, without isolation of the isothiocyanate, by the addition thereto of an aliphatic alcohol and an improved catalyst of the invention, preferably a tetraalkyl titanate or tetraalkyl zirconate catalyst. The reaction mixture is then heated, generally to a temperature of about 100° C. to about 120° C., preferably 110° C. to 120° C., for a period of about 3 to 6 hours. When the reaction is completed, any unreacted alcohol is stripped in vacuo.

The water content of both reactants, that is, the allyl isothiocyanate and the aliphatic alcohol sould be as low as possible to preclude hydrolysis of the catalyst. In general, the amount of water present in the reaction mixture should be less than about 0.25%.

The examples which follow further define and illustrate the scope of the invention.

EXAMPLE 1

A mixture of 0.25 mole of allyl isothiocyanate and 0.5 mole of isobutyl alcohol was heated under nitrogen to 110° C. in the presence of 0.4 gram/mole of allyl isothiocyanate of (a) tetra-n-butyl titanate and (b) ferric acetylacetonate. The reaction was followed and percent conversion to N-allyl-O-isobutyl thionocarbamate determined by gas chromatography. Results are given in Table I.

TABLE I

| Reaction of Allyl Isothiocyanate and Isobutyl Alcohol (mole ratio 1:2) | | | |
|---|---|---|---|
| | Percent Conversion | | |
| Catalyst | 1 Hr | 3 Hrs | 6 Hrs |
| None | — | — | 52.4 |
| Tetra-n-butyl titanate | 70.7 | 97.7 | 99.3 |
| Ferric acetylacetonate | 75.3 | 81.5 | 85.0 |

The data in Table I illustrate the significantly higher degree of conversion after 3 and 6 hours when tetrabutyl titanate is used as the catalyst compared with the known ferric acetylacetonate.

EXAMPLE 2

The procedure of Example 1 was followed except that the mole ratio of allyl isothiocyanate to isobutyl alcohol was 1:1, and the effect of catalyst and catalyst concentration was evaluated. Data are given in Table II.

TABLE II

| Reaction of Allyl Isothiocyanate and Isobutyl Alcohol (mole ratio 1:1) | | | | | |
|---|---|---|---|---|---|
| | Grams/ | Percent Conversion | | | Per- |
| Catalyst | Mole RNCS | 1 Hr | 3 Hrs | 6 Hrs | cent Purity |
| None | — | — | — | 33 | — |
| Tetrabutyl titanate | 0.4 | — | 97.4 | 97.3 | 89.4 |
| Tetrabutyl titanate | 0.2 | 84.6 | 96.8 | 96.5 | 88.3 |

TABLE II-continued

Reaction of Allyl Isothiocyanate and Isobutyl Alcohol (mole ratio 1:1)

| Catalyst | Grams/ Mole RNCS | Percent Conversion 1 Hr | Percent Conversion 3 Hrs | Percent Conversion 6 Hrs | Percent Purity |
|---|---|---|---|---|---|
| Tetraisopropyl titanate | 0.4 | — | 96.3 | 96.1 | 87.5 |
| Tetra-2-ethylhexyl titanate | 2.0 | — | 96.4 | 95.7 | 85.4 |
| Ferric acetylacetonate | 0.4 | 62.6 | 63.7 | 67.5 | 40.8 |
| Ferric acetylacetonate | 2.0 | 82.8 | 84.8 | 86.5 | 56.9 |
| Dibutyl Tin Dilaurate | 2.0 | 62.1 | 76.1 | 87.4 | 57.1 |

The data given in Table II illustrate the following: at a mole ratio of allyl isothiocyanate to isobutyl alcohol of 1:1, the tetraalkyl titanate catalysts provide (1) higher conversion, (2) higher purity product in (3) a shorter reaction time using (4) lower catalyst concentration than either of the known catalysts—ferric acetylacetonate or dibutyl tin dilaurate. The data also show that even at higher concentration the known catalysts provide the N-allyl-O-isobutyl thionocarbamate in very low purity.

EXAMPLE 3

Reaction of Allyl Isothiocyanate with n-Propyl Alcohol

The procedure of Example 2 was followed except that 0.25 mole of n-propyl alcohol was used instead of 0.25 mole of isobutyl alcohol. Tetra-n-butyl titanate was used at a concentration of 0.1 gram (0.4 gram per mole of allyl isothiocyanate). After heating for 6 hours at 110° C., a conversion of 97.3% to N-allyl-O-n-propyl thionocarbamate, having a purity of 90.2%, was realized.

EXAMPLE 4

Reaction of Allyl Isothiocyanate with 1-Pentanol

The procedure of Example 2 was followed except that 0.25 mole of 1-pentanol was used instead of 0.25 mole of isobutyl alcohol. Tetra-n-butyl titanate was used at a concentration of 0.1 gram (0.4 grams/mole of allyl isothiocyanate). After heating for 6 hours at 110° C., a conversion of 97% to N-allyl-O-pentyl thionocarbamate, having a purity of 77.5%, was realized.

EXAMPLE 5

Reaction of Allyl Isothiocyanate with Ethanol

The procedure of Example 2 was followed except 0.25 mole of ethanol was used instead of 0.25 mole of isobutyl alcohol. Tetra-n-butyl titanate was used at a concentration of 0.3 gram (1.2 grams/mole of allyl isothiocyanate). After heating at reflux (87° C.) for 13.5 hours, the reaction afforded a 93.3% conversion to N-allyl-O-ethyl thionocarbamate, having a purity of 81.9%.

EXAMPLE 6

The reaction of Example 5 was repeated except that ethanol was slowly added, over a period of 3 hours, to the allyl isothiocyanate and tetrabutyl titanate at 110° C. The reaction mixture was heated for an additional 2.5 hours following the addition of the ethanol, giving a conversion of 96.5% to N-allyl-O-ethyl thionocarbamate, having a purity of 85.4%.

EXAMPLE 7

Reaction of Allyl Isothiocyanate with Isobutyl Alcohol (mole ratio 1:1)

Several tetraalkyl titanate catalysts and one tetraaryl titanate catalyst were evaluated at a level of 0.4 gram per mole of allyl isothiocyanate in the reaction of allyl isothiocyanate and isobutyl alcohol at 110° C. The course of the reaction was followed by gas chromatography as described in Example 1. Data are given in Table III.

TABLE III

| Catalyst | Gm/Mole RNCS | Reaction Time, Hrs | Percent Conversion | Percent Purity |
|---|---|---|---|---|
| Tetramethyl titanate | 0.4 | 5 | 97.2 | 90.3 |
| Tetraethyl titanate | 0.4 | 1.75 | 79.0 | — |
| Tetraethyl titanate | 0.4 | 5 | 98.0 | 89.0 |
| Tetracresyl titanate | 0.4 | 4 | 97.1 | — |
| Tetracresyl titanate | 0.4 | 6 | 98.3 | 91.7 |
| Diisopropoxybis (2,4-pentane dionato) Titanium (IV) | 0.4 0.4 | 4 6 | 92.4 96.2 | — 82.3 |
| Niobium phenoxide | 1.2 | 6.5 | 87.5 | 64.4 |
| Lanthanum isopropoxide | 1.2 | 5.75 | 95.1 | 75.7 |
| Vanadyl n-butylate | 1.2 | 1.5 | 87.9 | — |
| Vanadyl n-butylate | 1.2 | 5 | 93.7 | 72.3 |

EXAMPLE 8

Preparation of N-Allyl-O-Isobutyl Thionocarbamate

A solution of 745.6 grams (15 moles) of sodium cyanide and 12 grams (0.037 mole) of tetra-n-butyl ammonium bromide in 1400 ml of water was treated with 483.3 grams (15.08 moles) of sulfur portionwise over 30–40 minutes, the temperature rising to 113° C. After stirring for 30 minutes, the solution was cooled to less than 40° C. Allyl chloride (1263 grams, 16.5 moles) was added over 15–20 minutes and the reaction mixture refluxed for 3.5 hours, the temperature reaching 90° C. At this point conversion was 99+%. Water (1100 ml) was added and the mixture cooled to 40° C. The aqueous phase was separated from the organic phase and the excess allyl chloride and trace amounts of water were stripped in vacuo (22 in. Hg) to a temperature of 100° C. Water content at this point was 0.02%. Isobutyl alcohol (1136 grams, 15 moles) and tetran-butyl titanate (9 grams, 0.026 mole) were added and the mixture was heated at 110° C. for 6.5 hours to a conversion of 96.1%. Unreacted isobutyl alcohol was stripped, yielding 2280 grams (87.9% yield) of N-allyl-O-isobutyl thionocarbamate having a purity of 87%.

EXAMPLE 9

Preparation of N-Allyl-O-Isobutyl Thionocarbamate

The procedure of Example 8 was followed except that 1.2 grams/mole of allyl isothiocyanate of a zirconium n-butoxide butanol complex

$(n\text{-}C_4H_9)_4Zr\cdot C_4H_9OH$ was used. Reaction with isobutyl alcohol at 110° C. gave a 96.7% conversion after 3.5 hours and 98.4% conversion after 5.5 hours to N-allyl-O-isobutyl thionocarbamate having a purity of 86.6%.

Examples 8 and 9 illustrate the preparation of N-allyl-O-alkyl thionocarbamates according to a unitary process, described hereinabove, which includes the initial preparation of an allyl isothiocyanate in high yield by the reaction of an allyl halide with an aqueous solution of an alkali metal or ammonium thiocyanate. Example 9 illustrates the use of a tetraalkyl zirconate catalyst.

What is claimed is:

1. In a process for the preparation of N-allyl-O-alkyl thionocarbamates by reaction of an allyl isothiocyanate with an alcohol in the presence of a catalytic amount of a catalyst, the improvement comprising: said catalyst being a compound having the general formula:

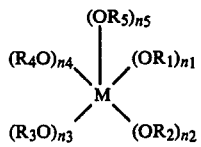

wherein $R_1$, $R_2$, $R_3$, $R_4$, and $R_5$ are individually selected from alkyl or aryl or mixtures thereof, M is a metal selected from Group III B, IV B, or V B of the Periodic Table of the Elements, n is the integer 0 or 1, and provided that the sum of $n_1$, $n_2$, $n_3$, $n_4$, and $n_5$ equals the valence of the metal; said improvement thereby providing improved catalysis for said reaction.

2. The improved process of claim 1 wherein said metal is selected from Group IV B of the Periodic Table of the Elements.

3. The improved process of claim 2 wherein said metal is titanium or zirconium.

4. The improved process of claim 3 wherein said metal is titanium.

5. The improved process of claim 3 wherein said metal is zirconium.

6. The improved process of claims 1, 2, 3, 4, or 5 wherein R is an alkyl group containing from 1 to 20 carbon atoms.

7. The improved process of claim 6 wherein R is an alkyl group containing from 1 to 8 carbon atoms.

8. The improved process of claim 4 wherein said compound is selected from tetra-n-butyl titanate, tetra-isopropyl titanate, tetra-2-ethylhexyl titanate, and mixtures thereof.

9. The improved process of claim 8 wherein said isothiocyanate has the general formula:

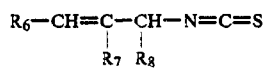

and said alcohol has the general formula:

wherein $R_6$, $R_7$, and $R_8$ are individually selected from hydrogen, alkyl, aryl and substituted aryl; $R_9$ is alkyl, wherein said alkyl chain may contain a hetero atom selected from O, S, and N; and m is the integer 1 or 2.

10. The improved process of claim 9 wherein $R_6$, $R_7$, $R_8$, and $R_9$ are alkyl of 1 to 20 carbon atoms.

11. The improved process of claim 10 wherein said catalyst is used in an amount of about 0.1 to 1.0 mole percent, based on the allyl isothiocyanate.

12. The improved process of claim 11 wherein $R_5$ is isobutyl and m is 1.

* * * * *